(12) United States Patent
Dyer et al.

(10) Patent No.: US 6,384,227 B2
(45) Date of Patent: May 7, 2002

(54) RACEMISATION PROCESS FOR USE IN THE MANUFACTURE OF LEVOBUPIVACAINE AND RELATED PIPERIDINECARBOXANILIDE ANAESTHETIC AGENTS

(75) Inventors: Ulrich Conrad Dyer; Marianne Langston; Martin Woods, all of Cambridge (GB)

(73) Assignee: Darwin Discovery Ltd. (GB)

(*) Notice: Subject to any disclaimer, the term of this patent is extended or adjusted under 35 U.S.C. 154(b) by 0 days.

(21) Appl. No.: 09/740,152

(22) Filed: Dec. 18, 2000

Related U.S. Application Data

(63) Continuation of application No. 09/396,628, filed on Sep. 14, 1999, which is a continuation of application No. 08/875,636, filed as application No. PCT/GB95/00067 on Jan. 13, 1995, now abandoned.

(30) Foreign Application Priority Data

Jan. 18, 1995 (GB) .............................. 9501071

(51) Int. Cl.[7] ............................................ C07D 211/60
(52) U.S. Cl. ....................................... 546/225
(58) Field of Search .......................................... 514/225

(56) References Cited

FOREIGN PATENT DOCUMENTS

FR 2301498 9/1976
WO 9609290 3/1996

OTHER PUBLICATIONS

Scott et al. (1993) "Synthesis of enantiomerically pure drugs" In Drug Stereochemistry, ed. Wainer, Macel Dakker Pub. pp. 183–187.
Pine "Organic Chemistry" CGraw–Hill, Inc. pp. 98–102 (1987).
Fyhr, P., C. Hogstroem (1988) "A Preformulation Study on the Kinetics of the Racemisation of Ropivacaine Hydrochloride" *Acta Pharmaceutica Suecica* 25(3):121–132.
Yadada, S. et al. (1983) "Method for the Racemisation of Optically Active Amino Acids" *J. Org. Chem.* 48:843–846.
Smith, G.G. et al. (1978) "Rate of Racemisation of Amino Acids and Their Significance to Geochronology" *J. Org. Chem.* 43(i), pp. 1–5.
Shiraiwa, T. et al. (1991) "Transformation of Proline and 2–Piperdinecarboxylic Acid via Formation of Salts with Optically Active Tartaric Acid" *Bull. Chem. Soc. Jpn.* 64:3251–3255.
Sato, M. et al. (1970) "Racemisation of Amino Acids and Their Derivatives" *Chem. Pharm. Bull.* 18(9):1794–1798.

*Primary Examiner*—Ceila Chang
(74) *Attorney, Agent, or Firm*—Saliwanchik, Lloyd & Saliwanchik

(57) ABSTRACT

An optically-enrichedpiperidine-2-carboxanlidecompound, in which the piperidine is optionally N-alkylated, is racemized by heating the compound in an aqueous medium, provided that the medium includes an organic co-solvent if the compound is N-alkylated. This process is particularly valuable, in conjunction with a resolution process, for the manufacture of levobupivacaine.

8 Claims, No Drawings

RACEMISATION PROCESS FOR USE IN THE MANUFACTURE OF LEVOBUPIVACAINE AND RELATED PIPERIDINECARBOXANILIDE ANAESTHETIC AGENTS

CROSS-REFERENCE TO A RELATED APPLICATION

This application is a continuation of application Ser. No. 09/396,628, filed Sep. 14, 1999; which is a continuation of application Ser. No. 08/875,636, filed Jul. 16, 1997, now abandoned which is a 371 of PCT/GB95/00067, filed Jan. 13, 1995.

FIELD OF THE INVENTION

This invention relates to the racemisation of optically-enriched piperidine-2-carboxanilides. In particular, the process is suitable for use in the manufacture of levobupivacaine and related piperidinecarboxanilide anaesthetic agents.

BACKGROUND OF THE INVENTION

Compounds of formula 1

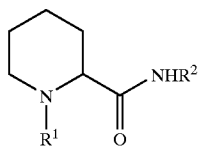

wherein $R^2$ is 2,6-dimethylphenyl and $R^1$ is methyl (mepivacaine), n-propyl (ropivacaine as S-enantiomer) or n-butyl (bupivacaine) are widely used as local anaesthetics. The corresponding compound when $R^1$ is H is a useful intermediate.

Biological studies have shown that the (S)-enantiomers of such N-alkyl-piperidine-2-carboxanilides display lower cardiotoxicity than the corresponding racemates, whilst maintaining the same anaesthetic potency, and are therefore more beneficial for clinical uses. Thus there is a requirement for efficient processes to manufacture compounds of formula 1 in the form of single enantiomers. For this purpose, conventional resolution approaches invariably afford up to 50% of the unwanted enantiomer. To improve atom utilisation in such processes, it is desirable to recycle the unwanted enantiomer by effecting its racemisation in order to provide material suitable for subsequent resolution.

Friberger et al, Acta. Pharm. Suec. (1971) 8: 361–364, report a study of the solubility and partition coefficients of the racemates and enantiomers of mepivacaine and bupivacaine. It is reported that racemic bupivacaine is more soluble than the isomers at a pH above 6. All of the compounds tested have solubilities decreasing to low levels, especially for bupivacaine, at pH values approaching neutrality.

Fyhr et al, Acta.Pharm.Suec. (1988) 25:121–132, report the racemisation of optically-enriched ropivacaine hydrochloride in dilute aqueous solution at pH 1–6 and 80–130° C. HCl or citric acid was: present, in order to establish the pH. The conclusions of this pre-formulation stability study were that the racemisation involves hydroxyl ion-catalysed racemisation of the N-protonated species. This study provides no useful indication as to how to conduct racemisation as such, and does not suggest any volume-efficient commercial process.

SUMMARY OF THE INVENTION

The present invention is based on the surprising discovery that piperidine-2-carboxanilides, including compounds of formula 1 wherein $R^1$ is H, methyl, n-propyl or n-butyl and $R^2$ is 2,6-dimethylphenyl, undergo rapid racemisation when heated in aqueous solution, provided that an organic cosolvent is present when $R^1$ is not H. The practical nature of this discovery is evident in that much more concentrated systems can be used than in the prior art.

Whereas, at concentrations of 30 mg/ml, at a pH above 5, the use of conditions otherwise specified by Fyhr et al lead to complete inhibition of racemisation of ropivacaine and bupivacaine, the rate of racemisation can be increased, under the conditions used in this invention, with increasing pH of the solution. Racemisation occurs most efficiently at a pH greater than 6, without loss of solubility, which means that no acid need be added.

DESCRIPTION OF THE INVENTION

The reaction can be carried out in water alone, when $R^1$ is H. In this case, a preferred embodiment of the invention is the racemisation of optically-enriched 2',6'-dimethylpiperidine-2-carboxanilide (1: $R^1$=H, $R^2$=2,6-dimethylphenyl).

Alternatively, for N-alkylpiperidine compounds of formula 1, the reaction is carried out in the presence of an organic cosolvent such as an alcohol or polyol, e.g. ethylene glycol thus allowing solutions of higher concentration to be used, than in the prior art. A preferred embodiment of this aspect of the invention is the racemisation of optically-enriched bupivacaine in ethylene glycol containing 10% v/v water. The presence of salt forms of compounds of formula 1 does not impede the efficiency of the racemisation process.

The reaction conditions may comprise heating, as desired. Suitable conditions will depend on the nature of the reactants, but can be readily chosen by those skilled in the art.

In summary, the present invention establishes simple and economical processes for the racemisation of piperidine-2-carboxanilides, in either neat aqueous media or aqueous media combined with inert organic cosolvents. The invention is particularly suited to the optimum utilisation of unwanted enantiomer in the preparation of enantiopure therapeutic agents, and therefore in practice the starting material will usually be richer in the (R)-enantiomer. When $R^1$ is H, a compound of formula 1 is an intermediate en route to anaesthetic agents. When $R^1$ is n-butyl, the present invention is of particular utility for preparing (S)-bupivacaine, in conjunction with a resolution process, e.g. that described in PCT/GB95/02513 and South African Application No. 95/8993.

The following Examples illustrate the invention.

EXAMPLE 1

(S)-2',6'-Dimethylpiperidine-2-carboxanilide (>99% ee, 155 mg, 0.67 mmol) was dissolved in water (14.5 ml). The pH was measured to be 9.97. The solution was heated under reflux for 19 hours. Aqueous ammonia (28% w/v; 1 ml) was added to the cooled solution and the mixture extracted with ethyl acetate (2×20 ml). The combined organic layers were dried with magnesium sulphate and the solvent removed under reduced pressure to give a white crystalline solid (128 mg). Analysis by chiral HPLC showed this to be racemic 2',6'-dimethylpiperidine-2-carboxanilide.

EXAMPLE 2

A mixture of (S)-bupivacaine (>99% ee, 1.5 g mmol), ethylene glycol (13.5 ml) and water (1.5 ml) was heated at 138° C. for 9 hours. On cooling to ambient temperature crystallisation of a solid occurred. The solid was filtered to give a quantitative yield of bupivacaine which was shown by chiral HPLC analysis to be a 52:48 mixture of (S)-bupivacaine and (R)-bupivacaine.

EXAMPLE 3

(S)-Bupivacaine (>99% ee, 0.27 g, 0.94 mmol) and (S)-bupivacaine (−)-tartrate (2:1 salt, 0.23 g, 0.32 mmol) were heated at 150° C. in propan-2-ol (2.5 ml) and water (2.5 ml) in a sealed vessel for 22 hours. A portion of solution was removed, basified with 28% aqueous ammonia and extracted into heptane. The organic solution was dried with magnesium sulphate and the solvent removed under reduced pressure. The residue was shown by chiral HPLC to be a 63:37 mixture of (S)-bupivacaine and (R)-bupivacaine.

We claim:

1. A process for the racemisation optically-enriched compound

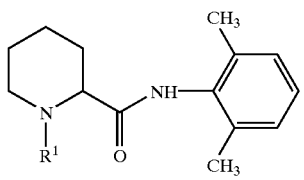

wherein $R^1$ is $C_{1-6}$ alkyl, the compound being in free base form, which comprises heating the compound in an aqueous medium which includes an organic cosolvent, and recovering the product that is precipitated, on cooling; wherein the concentration of the compound in the medium is at least 30 mg/ml.

2. The process according to claim 1, wherein said compound is enriched in the (R)-enantiomer.

3. The process according to claim 1, wherein the cosolvent is an alcohol or polyol.

4. The process according to claim 3, wherein the cosolvent is an ethylene glycol.

5. The process according to claim 1, wherein the concentration of the compound in the medium is at least 100 mg/ml.

6. The process according to claim 1, wherein $R^1$ is n-butyl, for preparing bupivacaine of diminished optical purity.

7. The process according to claim 1, wherein $R^1$ is n-propyl.

8. A process for preparing (S)-bupivacaine, which comprises resolving a mixture of enantiomers of bupivacaine, separating (S)-bupivacaine, and racemising residual (R)-bupivacaine, prior to further resolution; wherein said racemisation of residual (R)-bupivacaine comprises heating the compound in an aqueous medium which includes an organic cosolvent, and recovering the product that is precipitated, on cooling.

* * * * *

UNITED STATES PATENT AND TRADEMARK OFFICE
CERTIFICATE OF CORRECTION

PATENT NO.     : 6,384,227 B2                                                           Page 1 of 1
DATED          : May 7, 2002
INVENTOR(S)    : Ulrich Conrad Dyer, Marianne Langston and Martin Woods It is certified that error appears in the above-identified patent and that said Letters Patent is hereby corrected as shown below:

<u>Column 3,</u>
Line 18, "racemisation optically" should read -- racemisation of an optically --.

Signed and Sealed this

Sixth Day of May, 2003

JAMES E. ROGAN
*Director of the United States Patent and Trademark Office*